United States Patent [19]

Wysong

[11] 4,435,383

[45] Mar. 6, 1984

[54] SLOW RELEASE PESTICIDE FORMULATIONS

[75] Inventor: Robert D. Wysong, Wilmington, Del.

[73] Assignee: E. I. Du Pont de Nemours and Company, Wilmington, Del.

[21] Appl. No.: 284,700

[22] Filed: Jul. 22, 1981

Related U.S. Application Data

[63] Continuation-in-part of Ser. No. 184,209, Sep. 5, 1980, abandoned.

[51] Int. Cl.$^3$ .................... A01N 25/10; A61K 31/74
[52] U.S. Cl. ........................................ 424/78; 424/32; 525/113
[58] Field of Search .................... 424/78, 32; 525/113

[56] References Cited

U.S. PATENT DOCUMENTS

| | | | |
|---|---|---|---|
| 3,154,460 | 10/1964 | Graner et al. | 424/32 |
| 3,242,051 | 3/1961 | Hiestand et al. | 424/78 |
| 3,880,811 | 4/1975 | Kaupp et al. | 525/113 |
| 4,007,258 | 2/1977 | Cohen et al. | 424/22 |
| 4,153,682 | 5/1979 | Ackers | 424/78 |

FOREIGN PATENT DOCUMENTS 786777 6/1968 Canada.
4758 10/1979 European Pat. Off..

OTHER PUBLICATIONS

Tocker, U.S. Ser. No. 92,330, filed 11/8/79.
Coppedge et al., *J. Econ. Ent.*, 68 (4), 508–510 (1975).
Chem. Abstracts, 79, 14455v, 110 & 14457v, 111 (1973).
Subramanian et al., "Antifouling Polymers: Room-temperature-Curing Organotin Polymers".
Subramanian et al., "Properties of Organotin Polyesters Crosslinked by Cycloaliphatic Epoxides".
Somasekharan et al., "Structure, Mechanism and Reactivity of Organotin Carboxylate Polymers".

*Primary Examiner*—Delbert R. Phillips
*Assistant Examiner*—F. T. Moezie

[57] ABSTRACT

This invention relates to a one-phase, solid controlled release pesticidal composition consisting essentially of a pesticide in homogeneous combination with a crosslinked copolymer prepared from hydrophobic monomers, selected from styrene and α-methyl styrene, and carboxylic acid-containing monomers.

30 Claims, No Drawings

SLOW RELEASE PESTICIDE FORMULATIONS

This application is a continuation-in-part of co-pending application U.S. Ser. No. 184,209, filed Sept. 5, 1980, now abandoned.

BACKGROUND OF THE INVENTION

Controlled release pesticidal compositions offer several possible advantages over conventional compositions. First, they are more economical, as fewer pesticide applications to the crop are necessary. Controlled release compositions offer safety to the environment by preventing pesticide overuse and run-off or soil (translocation) leaching into unwanted neighboring areas such as water ways. They also offer safety to the crop in instances when large doses of conventional formulations are phytotoxic and offer safety to workers applying pesticides in the field by reducing human toxicity. Finally, controlled release compositions allow the effective use of pesticides which are too rapidly degraded or volatilized in conventional formulations (i.e., conventional pesticides with very low residual activity).

Many types of controlled release pesticidal compositions, however, suffer from disadvantages as well. One type, microcapsules, consist of an external polymeric barrier and an internal active core. Although microcapsules can provide effective controlled release, they are expensive to produce as solvents are necessary, there are process difficulties in isolating intact, non-leaking capsules, and recycle is difficult. In addition, the microcapsules can be difficult to formulate. It is difficult to produce capsules small enough for a wettable powder formulation. Even when small capsules are made, they are often inefficient as they tend to roll off plant surfaces due to their spherical shape. In addition, microcapsules cannot easily be made into granular formulations.

Another known type of controlled release pesticidal composition, overcoated carriers, consists of a porous, inert, solid core (e.g. clay particles or a porous plastic) into which the active ingredient is adsorbed, the core then being overcoated with a barrier layer (polymers or waxes). These compositions suffer the same general disadvantages as microcapsules. They are expensive to produce because solvent processes are necessary, and careful overcoating is needed to produce a product with reproducible release rates. They can also be difficult to formulate. For example, overcoated carriers are usually unsuitable as wettable powders because particles agglomerate during the overcoating step and are too large for such a formulation.

The one-phase controlled release pesticidal compositions described in the art also suffer certain advantages. Many are prepared via expensive solvent processes. Nearly all are not very friable and are thus unsuitable for milling to a fine wettable powder. Many such compositions undergo phase separation during processing (e.g. grinding to particles) and thus lose much of their ability to control the release of the pesticide.

Very few of the known one-phase compositions provide for a homogeneous matrix-active ingredient combination. In one type of homogeneous composition, the active ingredient is chemically bound to the matrix, the matrix generally being a polymer with pendant, reactive functional groups. These compositions are expensive to produce and are also expensive to market as the compositions must often be registered as new compounds and extensively tested before use. Furthermore, the choice of pesticides is very limited, since only those with reactive functional groups may be used.

Other known one-phase, homogeneous compositions do not involve chemically-bound active ingredients but utilize barriers which do not provide effective controlled release for most pesticides. Many of these compositions will also undergo phase separation upon storage or will cake when in particulate form.

There thus exists a clear need for controlled release pesticidal compositions which avoid the problems inherent in the prior art compositions.

SUMMARY OF THE INVENTION

A new, one-phase, solid controlled release pesticidal composition has now been discovered which consists essentially of about 5 to 75 weight percent of pesticide in homogeneous combination with a cross-linked copolymer prepared from
 (a) about 40 to 80% by weight of a hydrophobic barrier monomer selected from styrene and α-methyl styrene, and
 (b) about 20 to 60% by weight of one or more unsaturated mono- or di-carboxylic acids in which all or part of the carboxyl groups are in the anhydride form,
where 5 to 95% of the available carboxyl groups in said copolymer are cross-linked with a cross-linking agent selected from (i) one or more aromatic polyfunctional amines, optionally in combination with one or more aromatic polyfunctional isocyanates, aliphatic polyfunctional amines, polyols or polyfunctional epoxides, or (ii) one or more aromatic polyfunctional isocyanates, optionally in combination with one or more aromatic polyfunctional amines, aliphatic polyfunctional amines, polyols or polyfunctional epoxides. These novel compositions offer several advantages over prior art controlled release compositions. First, the process for preparing the compositions is comparatively inexpensive as a melt process is used rather than a solvent process. The process yields products whose release rates are reproducible from batch to batch, since the steps of incorporation of the active ingredient into the polymer and the shaping of the composition into solid forms are independent of one another. Finally, off-specification product can easily be recycled.

Another advantage of these novel compositions is that they can be formulated in a variety of ways, for example, wettable powders, granules and strips. They offer a special advantage over prior art compositions in their ability to be formulated into wettable powders. For use as wettable powders, these compositions can be ground to yield fine, irregularly shaped particles which exhibit excellent adherence to plant surfaces. In addition, these wettable powders exhibit little caking, even upon aging.

A final advantage of these compositions is that the pesticide is not chemically bound to the copolymer matrix. Thus, new product registration is not necessarily needed prior to marketing.

DETAILED DESCRIPTION OF THE INVENTION

The compositions of this invention contain about 5 to 75% by weight of one or more pesticides, preferably about 30 to 50% by weight. The lower limit on the amount of pesticide is set by the economics of use, and the higher limit is set by the retaining capability of the copolymer matrix. When compositions of highly active pesticides such as the sulfonylurea herbicides (e.g., 2-chloro-N-[(4-methoxy-6-methyl-1,3,5-triazin-2-yl)aminocarbonyl]benzenesulfonamide) are desired, even lesser amounts of pesticide may practically be used in preparing the compositions. Pesticides which can be used in these compositions include insecticides, nematicides, herbicides, fungicides, miticides and aphicides. The following are examples of suitable pesticides although many others are also useful.

| Pesticidal Type | Chemical Type | Examples |
|---|---|---|
| Insecticides | carbamates | methomyl, carbaryl, carbofuran, aldicarb, |
| | organo thiophosphates | EPN, isofenphos, isoxathion chlorpyrifos, chlormephos |
| | organo phosphates | terbufos, monocrotophos, terachlorvinphos |
| | perchlorinated organics | methoxychlor |
| | synthetic pyrethroids | fenvalerate |
| Nematicides | carbamates | oxamyl |
| Herbicides | triazines | metribuzin, hexazinone, atrazine |
| | sulfonylureas | 2-chloro-N—[(4-methoxy-6-methyl-1,3,5-triazin-2-yl)aminocarbonyl]-benzenesulfonamide |
| | uracils (pyrimidines) | lenacil, bromacil, terbacil |
| | ureas | linuron, diuron, siduron neburon |
| | acetanilides | alachlor, metolachlor |
| | thiocarbamates | benthiocarb (SATURN) triallate |
| | oxadiazol-ones | oxadiazon |
| | phenoxyacetic acid | 2,4-D |
| | diphenyl ethers | fluazifop-butyl, acifluorfen, bifenox, oxyfluorfen |
| | dinitro anilines | trifluralin |
| | glycine phosphonates | glyphosate salts and esters |
| | dihalobenzonitrile | bromoxynil, ioxynil |
| Fungicides | nitrilo oximes | cymoxanil (curzate), |
| | imidazoles | benomyl, carbendazim, thiophanate-methyl |
| | triazoles | triadimefon |
| | sulfenamides | captan |
| | dithio carbamates | maneb, mancozeb, thiram, |
| | chloronated aromatics | chloroneb |
| | dichloro anilines | iprodione |
| Aphicides | carbamates | pirimicarb |
| Miticides | propynyl sulfites | propargite |
| | triazapentadienes | amitraz |
| | chlorinated aromatics | chlorobenzilate, tetradifan |
| | dinitrophenols | binapacryl |

The copolymer matrix is derived from a hydrophobic barrier monomer, namely styrene and/or α-methyl styrene, in combination with a monomer selected from one or more unsaturated mono- or di-carboxylic acids. The di-carboxylic acids are greatly preferred and of these, maleic is the most preferred. The styrene or α-methyl styrene portion of the copolymer acts as a barrier, preventing water penetration into the composition; styrene is especially preferred. The copolymer matrix may optionally contain up to about 10% of other hydrophobic monomers which will not substantially change the fundamental characteristics of the copolymer. Examples of such monomers are acrylonitrile, methacrylonitrile, and acrylates such as methylmethacrylate and ethylmethacrylate.

Examples of unsaturated di-carboxylic acids which can be used other than maleic acid include, for example, citraconic acid and itaconic acid. Examples of the mono-carboxylic acids include acrylic acid, crotonic acid, tiglic acid, angelic acid, methacrylic acid and isocrotonic acid. The anhydrides of these carboxylic acids can be used and are preferred as the anhydrides lend themselves more easily to cross-linking. The affinity of the pesticide for the acid or anhydride groups helps to provide a one-phase composition and also helps to provide controlled release of the pesticide.

Before cross-linking, the copolymer of styrene or α-methyl styrene and the mono- or di-carboxylic acid is preferably a low-molecular copolymer, in other words, in the range of 3,000 to 20,000. The copolymer more preferably has a molecular weight in the range of 4,000 to 15,000 and most preferably has a molecular weight in the range of 4,500 to 10,500. Low molecular weight polymers are preferred since their use results in more friable compositions, an advantage when particulate controlled release compositions are desired.

The copolymer contains about 40 to 80% by weight (before cross-linking) of styrene or α-methyl styrene. Copolymers with a styrene or α-methyl styrene content below 40% are generally too hydrophillic and tend to be poorer barriers to water. Copolymers with a styrene or α-methyl styrene content above 80% are not useful since the copolymer cannot be cross-linked to the desired extent and since the resulting composition lacks friability and tends to cake. The preferred styrene or α-methyl styrene content of the copolymer is in the range of about 50 to 75% by weight.

The copolymer is cross-linked with a cross-linking agent selected from (a.) an aromatic polyfunctional amine, optionally in combination with an aromatic polyfunctional isocyanate, an aliphatic polyfunctional amine, a polyol or a polyfunctional epoxide or (b.) an aromatic polyfunctional isocyanate, optionally in combination with an aromatic polyfunctional amine, an aliphatic polyfunctional amine, a polyol or a polyfunctional epoxide. It is believed that cross-linking enhances the slow-release characteristics of the compositions as it creates a network within the copolymer matrix, making it more difficult for the pesticide to escape and further promoting homogeneity.

Examples of suitable aromatic polyfunctional amines are ortho-, meta-, and para-phenylenediamine and 4,4'-methylenedianiline. (The term polyfunctional is used to mean a compound containing two or more functional groups, e.g., amino groups.) Examples of suitable aromatic polyfunctional isocyanates are toluene 2,4-diisocyanate, toluene 2,6-diisocyanate, PAPI (polymethylene polyphenylisocyanate) para-phenylene diisocyanate, meta-phenylene diisocyanate, naphthalene-1,5-diisocyanate, tetrachloro-m-phenylene diisocyanate, dichlorodiphenylmethane diisocyanate, 4,4'-diphenyl diisocyanate, bitolylene diisocyanate, diphenylether diisocyanates, and dimethyl diphenyl diisocyanates. The most preferred cross-linking agent is m-phenylenediamine as its use leads to compositions with greater friability.

The aromatic polyfunctional amines or aromatic polyfunctional isocyanates can be used as cross-linking agents either alone or in combination with additional cross-linking agents. The total cross-linkage should preferably contain at least 10% of the aromatic polyfunctional amine or isocyanate. The aromatic polyfunctional amines and isocyanates are preferably used alone or in combination with one another. The following are examples of polyols (compounds with two or more hydroxyl groups), aliphatic polyfunctional amines and polyfunctional epoxides which can be used in combination with the aromatic polyfunctional amine and isocyanate cross-linking agents.

Polyols:
  polypropylene oxide
  polypropylene glycol
  sorbitol
  dimethylolurea
  polybutylene oxide
  polyethylene glycol
  polyethylene oxide
  catechol
  resorcinol
  bisphenol A
  poly(urea formaldehyde)
  phenolic resins (e.g., novolak, resol)
  (polymeric condensation products between phenols and formaldehyde.)

Aliphatic polyfunctional amines:
  diethylenetriamine
  triethylenetetramine
  ethylenediamine
  guanidine
  hexamethylenetetramine (with moisture present)
  bis-amine-terminated polypropylene oxide
  ethanolamine
  diethanolamine
  triethanolamine Poly-functional epoxides:
  reaction product of epichlorohydrin plus bis-phenol A
  novolak-type epoxides
  $HCR_2CR_2H$—where R is

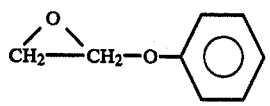

Rigid aliphatic epoxides such as:

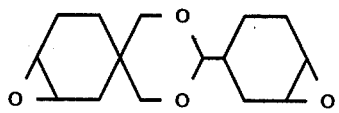

Approximately 5 to 95% of the total available carboxyl groups in the copolymer matrix are cross-linked with the cross-linking agents described above. (One anhydride group is equal to two available carboxyl groups.) It is preferable to cross-link between about 25 and 50% of the total available acid groups whether starting from the anhydride or free acid. The acid groups of the copolymer have an affinity for the pesticide and assist in retaining it within the solid composition, thus enhancing the slow-release characteristics of the solid. Thus, it is preferable to leave free a portion of the acid groups for compatibilizing the pesticide.

Compositions of this invention may be prepared by any methods producing homogeneous incorporation of a pesticide in a polymer matrix. Preferably, the pesticide and copolymer are heated in a kneading-type mixer such as a Sigma arm mixer (batch reaction) or in a melt extruder (continuous reaction) to a homogeneous melt. The mixture is heated to a temperature of about 60° to 150° C., preferably no higher than 120° C., keeping in mind that it is important not to exceed the decomposition temperature of the pesticide. The addition of the cross-linking agent can occur at any step during preparation, as determined by the pot-life of the cross-linking step. For example, the cross-linking agent can be mixed and heated with the copolymer and the pesticide in a batch reaction or can be added to a pre-melt of copolymer and pesticide in a continuous reaction.

On cooling, the resulting blend forms a rubbery mass which breaks up into crumbs at lower temperatures (e.g., below about 60° C.) The preferred particulate form of the composition described herein, finely ground powders, can be prepared by grinding, chipping or milling the crumbs to particles of the desired size. These particles are irregular in shape and, preferably, at least 90% of them are under 40 microns ($\mu$) in size in the longest dimension. More preferably, at least 90% of the particles are between 1 and 10$\mu$ in the longest dimension. Small particles are advantageous for several reasons. First, small particles are more likely to stay suspended in tank mixtures and will not clog screens and spray nozzles. Additionally, small particles, when sprayed onto plants, will be more greatly spread out over plant surfaces than larger particles and will thus provide more effective pest control. The determination of particle size can be done microscopically, or by techniques well known in the art, such as sieving, sedimentation, or by Coulter Counter.

Granular formulations of the composition of this invention can be prepared by dispersing minor amounts (less than or equal to 40% by weight of the total composition) of powdered carriers or diluents into the molten pesticide-copolymer mixture before cross-linking. The cooled, cross-linked mass is then ground to the desired granular size. Granular formulations can also be prepared by applying a liquid pesticidal-copolymer composition (before cross-linking and preferably in molten form, less preferably in solution) to preformed granular carriers such as granulated clays. Alternatively, the pesticide-copolymer composition can be formulated into granules, without added diluents, by coarse grinding the composition if in pulverulent form, or by preparing particulate shapes from conventional shotting, prilling, or extrusion/chipping operations.

The composition of this invention can also be formulated into shapes such as strips by extruding the molten blend or by molding the blend under heat and pressure to the desired shape.

As previously mentioned, the compositions of this invention are one-phase compositions, thus offering advantages in terms of economy and efficiency. The following test may be used to determine whether a composition according to this invention is one-phase.

TEST PROCEDURE

Stir and heat the following mixture on a steam bath in an open beaker under a hood:
  16.5 g SMA ®3000 A [poly(styrene/maleic anhydride), 75/25 weight %, MW 1900, sold by Arco Chemical Company]
  2.5 m-phenylenediamine
  1.0 g pesticide
  20–100 ml dry acetone or methylene chloride.

As stirring, heating and solvent evaporation continues, a one-phase molten mass results (by the time ca. 90% of the solvent is evaporated). Smear a sample of this mass (0.0001–0.01 inch thick layer) on a glass microscope slide. Place the coated slide in a nitrogen-purged chamber (such as an oven) and heat at 100° C. for 30–60 minutes. Upon cooling, remove the coated slide and examine for homogeneity using a microscope equipped with cross-polarizers. The absence of free pesticide as evidenced by the lack of two-phases (i.e., no separate crystals, particles, or oil) is an indication of homogeneity.

A preferred composition of this invention consists essentially of about 30 to 50 weight percent pesticide in homogeneous combination with a cross-linked copolymer of 75% styrene and 25% maleic anhydride cross-linked with about one equivalent (based on anhydride) of m-phenylenediamine. During preparation, this pesticide-copolymer composition forms a homogeneous melt at a low temperature and, on cooling, often provides a hard blend which can conveniently be ground.

An especially preferred composition contains methomyl as the pesticide. When applied to growing cotton plants in insecticidally effective amounts, this methomyl composition provides reduced phytotoxicity and increased residual activity compared to standard methomyl compositions.

This invention is further illustrated by the following examples.

EXAMPLE 1

A jacketed stainless steel sigma blade mixer (Readco Mixer, 6 qt. capacity) was charged with 1240 g methomyl, 1525 g SMA 3000A [poly(styrene/maleic anhydride) 75/25 weight %, MW 1900, sold by Arco Chemical Company], and 186 g meta-phenylenediamine [E. I. du Pont de Nemours and Company]. The dry mixture was mixed and heated with steam in the jacket to a melt temperature of 82° C. when the steam was turned off. With mixing continuing, the temperature rose to 103° C. whereupon cooling water (5° C.) was applied to the jacket. As the temperature decreased, the elastomeric mixture hardened and broke up into a dusty crumb. At 46° C., the polymer crumb was unloaded and found to contain 41% methomyl. The crumb was crushed in a Straub general purpose mill to a uniform granular size and blended with sodium lauryl sulfate, 2% by weight, sodium ligninsulfonate, 2% by weight, and fused silica, 2% by weight, to give a final concentration of 38% methomyl.

EXAMPLE 2

A batch of the formulated granules made as described in Example 1 was milled in an Alpine pin mill and then further ground in an 8″ air mill operating at a ring pressure of 100 psig. The resulting grey powder was determined, by Coulter Counter analysis in Isoton®II, to have an average particle size of 11μ where 90% of the particle population was 3–22μ (this particle size will hereafter be designated 11(3–22)μ.

EXAMPLE 3

Another batch of the formulated granules made as described in Example 1 was milled in a Bantam Mikropulverizer (hammer-mill) using a 0.01 herringbone screen and then in the air mill of Example 2. A powder was obtained, which by Coulter analysis was 6(3–12)μ.

EXAMPLE 4

The mixer used in Example 1 was charged with 2121 g of stock granules, made as described in Example 1, and 300 g methomyl. This mixture was heated with steam and mixed to reach a temperature of 80° when the mixture had formed a melt. In a separate 1 l stainless steel beaker, 446 g of Epon®828 (reaction product of epichlorohydrin and bis-phenol A, by Shell Chemical, having an average MW of 350–400 and a viscosity of 100–160 poises at 25° C. (Gardner-Holt)) and 79.5 g m-phenylene diamine (MPD) were heated on a steam bath to form a solution (60°–80° C.). This solution was added to the mixer, and the steam on the jacket was replaced by cool circulating water. A melt temperature of about 80°–85° C. was maintained for 10 minutes when the mixture began to turn rubbery. After one hour, rubbery, tacky crumbs had formed and were dumped from the mixer into a stainless steel tray, cooled and screened through a Stokes Granulator to give light green granules. These granules were fed to an 8″ airmill at ca. 20 lbs/hr. and the major portion converted to a powder 12(5–29)μ. This powder was converted to a wettable powder by drum tumbling with 0.5% Duponol®C.

EXAMPLES 5–14

The controlled release compositions listed in Table I were prepared as wettable powders (all 40% methomyl). The styrene/maleic anhydride (75/25 wt%)-methomyl mixtures were heated and stirred on a steam bath in a stainless steel beaker to prepare a homogeneous melt. To such molten mixtures the crosslinking agents were added and heating continued until the "set up time" when the melt became gelled or rubbery. The cooled melts were then ground in a laboratory hammer-mill to powders of the designated particle sizes.

An explanation of the abbreviations used in Table I follows the table.

TABLE I

| | | Reactants | | | | |
|---|---|---|---|---|---|---|
| Example No. | SMA[1] (moles) | $X_1$ (equivalents) | $X_2$ (equivalents) | $X_3$ (equivalents) | % X-linked | Particle Size (90% of range) |
| 5 | 3000 (0.0991) | Epon® 828 (0.0444) | MPD (0.0389) | — | 42 | (5–20) |
| 6 | 3000 (0.0765) | Epon® 1031 (0.0447) | MPD (0.0237) | — | 45 | (5–20) |
| 7 | 3000 (0.153) | Epon® 828 (0.118) | MPD (0.05) | DETA (0.02) | 47 | (10–40) |
| 8 | 3000 (.0102) | — | MPD (0.0869) | — | 43 | (5–20) |
| 9 | 3000 (0.102) | — | MPD (0.0509) | — | 20 | (5–30) |
| 10 | 3000 (0.102) | — | MPD (0.14) | — | 69 | (5–15) |
| 11 | 3000 | — | MPD | — | 93 | (4–15) |

TABLE I-continued

| Example No. | SMA[1] (moles) | Reactants X₁ (equivalents) | X₂ (equivalents) | X₃ (equivalents) | % X-linked | Particle Size (90% of range) |
|---|---|---|---|---|---|---|
| 12 | 3000 (0.102) | polypropylene glycol(Avg. M.W. 150) (0.0633) | MPD (0.0323) (0.19) (0.102) | — | 47 | (5-20) |
| 13 | 3000 (0.112) | Epon ® 828 (0.070) | 4,4'-methylene- dianiline (0.0358) | — | 48 | (5-20) |
| 14 | 3000 (0.071) | water (0.035) | toluene 2,4- diisocyanate (0.035) | — | 50 | (2-15) |

1. SMA refers to poly(styrene/maleic anhydride) prepared by Arco Chemical Co. SMA ®1000 contains ca. 50% maleic anhydride and SMA ®3000 ca. 25% by weight. Further characterization is as follows:

| SMA ® Resin | (No. Avg.) Molecular Weight | Melting Range, °C. | Acid No. | Solutions in Aqueous Ammonia | | | |
|---|---|---|---|---|---|---|---|
| | | | | 15% NVM* Viscosity (cps.) | Gardner Color | 20% NVM* Viscosity (cps.) | 30% NVM* Viscosity (cps.) |
| 1000 | 1600 | 150-170 | 480 | 17 | 1-2 | 28 | 50 |
| 3000 | 1900 | 115-130 | 275 | 52 | 1 | gel | gel |

*Non-Volatile Material

2. % X-linked indicates 100× the ratio of the total moles of cross-linking agent(s) to the total moles of available carboxyl groups in the SMA used. (There are two moles of carboxyl groups per mole of anhydride group.)
3. Equivalents based on maleic anhydride.
   Abbreviations and Tradenames Used in Table I
   MPD-m-phenylene diamine Epon 1031-(made by Shell Chemical; epoxide equivalent 210-240, m.p. ~80° C.)-HCR₂CR₂H where

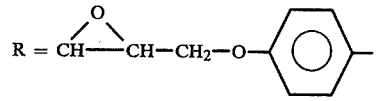

DETA-diethylene triamine

The particles made in Examples 2–12 and 14 were tested for release rates of methomyl in water. The sample weight of controlled release powder relative to that of water is so selected that when all the methomyl has been extracted ~1% by weight aqueous methomyl solution can result. The powder (plus 1% Duponol ®C) is placed in a capped jar and is stirred with a magnetic stirrer. Samples of the dispersion are withdrawn periodically, filtered, and the filtrate analysed for methomyl content. The results are given in Table II.

TABLE II

| Particles of Example # | Release Rate % Methomyl Extracted* Into Water After | | | |
|---|---|---|---|---|
| | 1 hr. | 1 day | 2 days | 7 days |
| 2 | 51 | 70 | — | 76 |
| 3 | 67 | 78 | 78 | 80 |
| 4 | 57 | 63 | 63 | 72 |
| 5 | 30 | 56 | | |
| 6 | 36 | 59 | 64 | 71 |
| 7 | 28 | 50 | 58 | |
| 8 | 52 | 68 | | |
| 9 | 54 | 69 | | |
| 10 | 60 | 69 | | |
| 11 | 68 | 75 | | |
| 12 | 31 | 49 | 54 | 66 |
| 13 | — | — | — | — |
| 14 | 54 | 65 | 68 | 76 |
| Methomyl Control | 100 | 100 | 100 | 100 |

*The percentage refers to the total amount of methomyl originally contained in the solid sample.

EXAMPLE 15

A 500 ml stainless steel beaker is charged with a pre-blended mixture of 115.6 g technical metribuzin (93%), 85.8 g SMA 3000A, and 10.6 g meta-phenylenediamine. The beaker is then heated on a hot plate to 120° C., held for 30 minutes, and then removed. During the heating cycle, the mixture melts and converts to a rubbery mass. After cooling, the polymer is broken up into granules and fed to a No. 1 Mikro-Pulverizer fitted with a 3/64" Herringbone screen. Further grinding is accomplished in a 2" air mill operating at a ring pressure of 70 psig to give a powder 2(1–5)μ, containing 51% metribuzin. When 2 g of this powder is suspended in 1 liter distilled water containing 0.4 g Duponol ®C, 42% of the metribuzin is released after one hour, 44% after two days and 51% after 14 days, by ultraviolet spectrophotometric analysis at 294 μm. By comparison, powdered technical metribuzin of similar particle size under the same conditions dissolved completely (i.e. 100% release) in 5 minutes.

EXAMPLE 16

7.5 g cymoxanil 7.4 MPD and 60 g of SMA 3000 were melted with intensive mixing and the temperature maintained at 110°–120° C. using a steam-water-jacketed mixer. Upon cooling, a brown transparent, brittle solid resulted. Samples of this solid were ground with 1% Duponol ®C and tested as follows:

| Average particle size (μ) | % Release Rate in water[1] after: | | |
|---|---|---|---|
| | 1 hr. | 1 day | 3 days |
| 14.7 | 50 | 53 | 55 |
| 4.0 | 50 | 58 | 66 |
| 2.1 | 61 | 71 | 75 |

[1] buffered to pH 3 with citrate to prevent cymoxanil decomposition.

EXAMPLE 17

The procedure of Example 21 was followed by using the following:

| | |
|---|---|
| SMA ® 3000A | 1892.2 g |
| technical oxamyl | 295.1 g |
| MPD | 54.0 g |
| Attaclay ® (an attapulgite clay produced by Engelhard Minerals and Chemicals Corp.) | 737.8 g |

A homogeneous melt which contained suspended clay particles resulted. After crumb formation and cooling, mixing and grinding within the sigma arm mixer was continued briefly and the contents discharged. A screened portion (−20 mesh/+40 mesh granules) of the discharged granules was tested for release rate in the usual way.

| | % Release Rate[1] in Water After | | | |
|---|---|---|---|---|
| | 30 min. | 3 hrs. | 1 day | 7 days |
| Control (tech. oxamyl absorbed on −20 mesh/+40 mesh Attaclay ® pellets) | 79 | 100 | 100 | 100 |
| Granules of Ex. 17 (9.9% oxamyl) | 14 | 31 | 41 | 50 |

[1] determined by refractive index measurements using a trace of Duponol ®C for wetting.

EXAMPLE 18

The procedure of Example 1 (but using a 3 qt. Sigma arm mixer) was used with the following:

| | |
|---|---|
| SMA ® 1000 | 649.0 g |
| MPD | 67.5 g |
| methomyl | 544.9 g |

Granules were formed as in Example 1 and were milled as in Example 2 to yield a wettable powder, 5(2–13)μ.

UTILITY

The preferred, particulate products of this invention are useful as pesticides when applied as a dust, water dispersible powder, or granules to plants or to soil. They are particularly useful for the control of pests attacking fruit, vegetable and legume crops.

For example, methomyl provides excellent control of a great many insect pests. When applied to foliage or fruiting bodies to be protected, however, some of it is taken up by the plant and subsequently degraded. This results in a loss of effectiveness in a few days. This is both inconvenient and uneconomical for certain uses since repeat applications are then needed. Repeated application and rapid plant absorption of methomyl leads to injury in some crops.

The particles of this invention retard absorption of methomyl by plant foliage, yet provide a ready source to the insect cuticle or stomach. Thus, when the particles of this invention are used, the methomyl remains available on the plant for insect control for a significantly longer period of time than when conventional formulations are used. This means that less methomyl is required to achieve a given level of insect control, resulting in less chance of plant injury, increased savings and reduced dispersal of insecticide into the biosphere. It also means that fewer applications are required thus providing an increase in convenience and a decrease in cost to the grower.

The methomyl-containing particles of this invention readily control pestiferous insects belonging to such orders as Lepidoptera, Homoptera, Hemiptera, Diptera and Coleoptera. More specifically, insects controlled by compositions of this invention include but are not limited to corn earworm (*Heliothis zea*), tobacco budworm (*Heliothis virescens*) southern armyworm (*Spodoptera eridania*), beet armyworm (*Spodoptera exigua*), soybean looper, (*Pseudoplusia includens*), green cloverworm (*Plathypena scabra*), codling moth (*Laspeyresia pomonella*), leafrollers of the family Tortricidae, alfalfa weevil (*Hypera postica*), Mexican bean beetle (*Epilachna varivestis*) and tarnished plant bug (*Lygus lineolaris*).

The insects are controlled by applying the particles in any convenient formulation to the locus of infestation, to the area to be protected, or to the pests themselves. For the control of insects in agricultural crops, the particle is generally applied to the foliage or other plant parts that are infested or which are to be protected. Effective amounts to be applied depend on the species to be controlled, its life stage, its size and location, the amount of rainfall, the time of year, moisture, temperature, type of application, and other variables. In general, 0.0625 to 4 kg/ha of the active ingredient may be required for insect control in agriculture with rates of 0.125 to 2 kg/ha usually being sufficient. Preferred rates for controlling pests in cotton are in the range of 0.125 to 1 kg/ha.

The particles of this invention may be used as is or may be formulated in conventional ways as dusts, wettable powders, granules or the like. They may be mixed with adjuvants such as diluents, carriers, or surfactants and spreader-stickers. Suitable diluents or carriers are minerals such as clays, talcs, pyrophyllites, hydrous aluminosilicates, fine silicas etc., and organic carriers like finely divided wood or shell flours. Surfactants such as wetting agents, dispersing agents, antifoam agents and the like may be used alone or in combination, especially if application from an aqueous spray is intended.

Application of the pesticides to plants may be made dry or by spraying from a water carrier. It is often desirable to use surfactants in water carrier to improve dispersion and wetting, and such surfactants can be added into the formulation or tank-mixed into the spray. Concentrated aqueous dispersions, containing up to 20% of the powders in the spray, or dilute dispersions containing as little as 80 ppm of powder, may be used.

The particles of this invention can be mixed with fungicides, bactericides, acaricides, nematicides, insecticides, or other biologically active compounds in order to achieve desired results with a minimum expenditure of time, effort and material. Amounts of these biologically active materials added for each part by weight of the compound of this invention may vary from about 0.05 to 25 parts by weight. Suitable agents of this type are well known to those skilled in the art. Some are listed below:

Fungicides:
methyl 2-benzimidazolecarbamate (carbendazim)
tetramethyl thiuram disulfide (thiram)
n-dodecylguanidine acetate (dodine)
manganese ethylenebisdithiocarbamate (maneb)
1,4-dichloro-2,5-dimethoxybenzene (chloroneb)
methyl 1-(butylcarbamoyl)-2-benzimidazolecarbamate (benomyl)
N-trichloromethylthiotetrahydrophthalimide (captan)
N-trichloromethylthiophthalimide (folpet)

Bactericides:
tribasic copper sulfate
streptomycin sulfate

Acaricides:
3,3-dimethyl acrylic acid, ester with 2-sec-butyl-4,6-dinitrophenol (binapacryl)
6-methyl-1,3-dithiolo[2,3-$\beta$]quinonolin-2-one (quinomethionate)
ethyl 4,4'-dichlorobenzilate (chlorobenzilate)
1,1-bis(p-chlorophenyl)-2,2,2-trichloroethane (dicofol)
bis(pentachloro-2,4-cyclopentadien-1yl) (dienochlor)
tricyclohexyltin hydroxide (cyhexatin)

Nematicides:
S-methyl 1-(dimethylcarbamoyl)-N-(methylcarbamoyloxy)-thioformimidate (oxamyl)
S-methyl 1-carbamoyl-N-(methylcarbamoyloxy)thioformimidate
N-isopropylphosphoramidic acid, O-ethyl-O'-[4-(methylthio)-m-tolyl]diester (fenamiphos)

Insecticides:
3-hydroxy-N-methylcrotonamide(dimethylphosphate)ester (mouscrotophos)
methylcarbamic acid, ester with 2,3-dihydro-2,2-dimethyl-7-benzofuranol (carbofuran)
O-[2,4,5-trichloro-$\alpha$-(chloromethyl)benzyl]phosphoric acid, O',O'-dimethyl ester (tetrachlorvinphos)
2-mercaptosuccinic acid, diethyl ester S-ester with thionophosphoric acid, dimethyl ester (malathion)
phosphorothioic acid, O,O-dimethyl, O-p-nitrophenyl ester (methyl parathion)
methylcarbamic acid, ester with $\alpha$-naphthol (carbaryl)
N'-(4-chloro-o-tolyl)-N,N-dimethylformamidine (chlordimeform)
O,O-diethyl-O-(2-isopropyl-4-methyl-6-pyrimidylphosphorothioate (diazinon)
octachlorocamphene (camphechlor)
O-ethyl O-p-nitrophenyl phenylphosphonothioate (EPN)
cyano(3-phenoxyphenyl)-methyl-4-chloro-$\alpha$-(1-methylethyl)benzeneacetate (fenvalerate)
(3-phenoxyphenyl)methyl($\pm$)-cis,trans-3-(2,2-dichloroethenyl)-2,2-dimethylcyclopropanecarboxylate (permethrin)
O-ethyl-S-(p-chlorophenyl)ethylphosphonodithioate (profenophos)
phosphorothiolothionic acid, O-ethyl-O-[4-(methylthio)phenyl]-S-n-propyl ester (sulprofos)

EXPERIMENT I

The foliage of Red Kidney bean plants in the two-leaf stage (8 days from planting) was sprayed to run-off with dispersions of the preparations of Examples 2–14 and 18. Dispersions were prepared by stirring appropriately weighed quantities of the powders in water containing sodium lauryl sulfate at 1:5000 and further diluting to 100 ml. At the stated interval after treatment, leaves were excised and placed in covered 10-cm Petri dishes along with moist filter paper to keep them turgid. Ten southern armyworm larvae were placed in each dish. The test units were kept in a room maintained at 77±2° F. and 55±5% relative humidity. Results were recorded at the end of two days and are listed below.

| Example | Spray Concentration (% active ingredient) | Mortality (% Dead) 2 days | Mortality (% Dead) 7 days |
|---|---|---|---|
| 2 | 0.01 | 100 | 100 |
|  | 0.005 | 95 | 100 |
|  | 0.0025 | 95 | 90 |
| 3 | 0.01 | 100 | 95 |
|  | 0.005 | 95 | 85 |
| 4 | 0.01 | 95 | 100 |
|  | 0.005 | 95 | 95 |
|  | 0.0025 | 85 | 85 |
| 5 | 0.01 | 100 | 100 |
|  | 0.005 | 100 | 100 |
| 6 | 0.01 | 100 | 100 |
|  | 0.005 | 100 | 100 |
| 7 | 0.01 | 95 | 100 |
|  | 0.005 | 95 | 100 |
| 8 | 0.01 | 100 | 100 |
|  | 0.005 | 95 | 100 |
| 9 | 0.01 | 100 | 100 |
|  | 0.005 | 100 | 100 |
| 10 | 0.01 | 95 | 100 |
|  | 0.005 | 100 | 95 |
| 11 | 0.01 | 100 | 85 |
|  | 0.005 | 75 | 80 |
| 12 | 0.01 | 100 | 100 |
|  | 0.005 | 80 | 90 |
| 13 | 0.01 | 95 | 100 |
|  | 0.005 | 80 | 100 |
| 14 | 0.01 | 100 | 100 |
|  | 0.005 | 100 | 100 |
| 18 | 0.01 | 100 | 100 |
|  | 0.005 | 100 | 100 |
| Methomyl Control | 0.01 | 15 | 0 |
| Untreated | 0 | 0 | 0 |

EXPERIMENT II

Potted cotton plants approximately 25 cm high having 3–4 true leaves were sprayed to run-off with aqueous dispersions of compositions of Examples 2 and 4–14 at 500 ppm active insecticide. The spray contained sodium lauryl sulfate at a concentration of 1:5000. Another set of plants was similarly treated with methomyl. After drying, plants were set out in the greenhouse and held for observation. After 6 days, the plants were rated for plant response: reddening of older leaves, slight puckering and black stippling of younger leaves. Rating is on the basis of 0–10, with 10 indicating total leaf involvement.

| Example | Plant Response Rating Experimental Composition | Unformulated Methomyl |
|---|---|---|
| 2 | 2 | 5 |
| 4 | 1.5 | 4 |
| 5 | 0.5 | 6 |
| 6 | 3 | 5 |
| 7 | 3 | 3 |
| 8 | 4 | 6 |
| 9 | 3 | 6 |
| 10 | 4 | 6 |

-continued

| Example | Plant Response Rating | |
|---|---|---|
| | Experimental Composition | Unformulated Methomyl |
| 11 | 4 | 6 |
| 12 | 4 | 5 |
| 13 | 5 | 5 |
| 14 | 2 | 3 |

What is claimed is:

1. A solid one-phase pesticidal composition containing no solvent and consisting essentially of about 5 to 75 weight % pesticide in homogeneous combination with a cross-linked copolymer prepared from
   (a) about 40 to 80% by weight of a hydrophobic barrier monomer selected from styrene and α-methyl styrene, and
   (b) about 20 to 60% by weight of one or more unsaturated mono- or di-carboxylic acids in which all or part of the carboxyl groups may be in the anhydride form, where 5 to 95% of the available carboxyl groups in said copolymer are cross-linked with a cross-linking agent selected from (i) one or more aromatic polyfunctional amines, optionally in combination with one or more aromatic polyfunctional isocyanates, aliphatic polyfunctional amines, polyols or polyfunctional epoxides.

2. The composition of claim 1 which contains about 30 to 50 weight % pesticide.

3. The composition of claim 1 where the carboxylic acid is a di-carboxylic acid.

4. The composition of claim 3 where the di-carboxylic acid is maleic acid.

5. The composition of claim 3 where the carboxylic acid is in anhydride form.

6. The composition of claim 5 where the carboxylic acid in anhydride form is maleic anhydride.

7. The composition of claim 1 where the hydrophobic monomer is styrene.

8. The composition of claim 1 where the cross-linking agent is an aromatic polyfunctional amine.

9. The composition of claim 8 where the cross-linking agent is m-phenylenediamine.

10. The composition of claim 1 where 25 to 50% of the available carboxyl groups are cross-linked.

11. The composition of claim 8 where 25 to 50% of the available carboxyl groups are cross-linked.

12. The composition of claim 9 where 25 to 50% of the available carboxyl groups are cross-linked.

13. The composition of claim 1 consisting essentially of about 30 to 50 weight percent pesticide in homogeneous combination with a cross-linked polymer prepared from:
    (a) about 75% styrene; and
    (b) about 25% maleic anhydride;
where about 50% of the available carboxyl groups are cross-linked with m-phenylenediamine.

14. The composition of claim 1 where the pesticide is methomyl.

15. The composition of claim 14 which contains about 30 to 50 weight % pesticide.

16. The composition of claim 14 where the carboxylic acid is a di-carboxylic acid.

17. The composition of claim 16 where the di-carboxylic acid is maleic acid.

18. The composition of claim 16 where the carboxylic acid is in anhydride form.

19. The composition of claim 18 where the carboxylic acid in anhydride form is maleic anhydride.

20. The composition of claim 14 where the hydrophobic monomer is styrene.

21. The composition of claim 14 where the cross-linking agent is an aromatic polyfunctional amine.

22. The composition of claim 21 where the cross-linking agent is m-phenylenediamine.

23. The composition of claim 14 where 25 to 50% of the available carboxyl groups are cross-linked.

24. The composition of claim 21 where 25 to 50% of the available carboxyl groups are cross-linked.

25. The composition of claim 22 where 25 to 50% of the available carboxyl groups are cross-linked.

26. A composition according to claim 1 consisting essentially of 30 to 50% methomyl in homogeneous combination with a cross-linked copolymer prepared from:
    (a) about 75% styrene and
    (b) about 25% maleic anhydride
where approximately 50% of the available carboxyl groups are cross-linked with m-phenylenediamine.

27. A composition according to claim 1 consisting essentially of 5 to 60% weight percent methomyl in homogeneous combination with a copolymer prepared from:
    (a) about 50 to 75% by weight of a hydrophobic barrier monomer selected from styrene and α-methyl styrene, and
    (b) about 25 to 50% of one or more unsaturated mono- or di-carboxylic acids in which all or part of the carboxyl groups may be in anhydride form,
where 5 to 95% of the available carboxyl groups in said copolymer are cross-linked with m-phenylenediamine.

28. A composition according to claim 12 in which the hydrophobic monomer is styrene, the unsaturated carboxylic acid-containing monomer is maleic anhydride.

29. A particulate composition of any of claims 1 to 28 in which at least 90% of the particles are under 40 microns in their largest dimension.

30. The composition of claim 29 in which at least 90% of the particles are between 1 to 10 microns in their largest dimension.

* * * * *